US007549336B2

(12) United States Patent  
Masyada

(10) Patent No.: US 7,549,336 B2
(45) Date of Patent: Jun. 23, 2009

(54) HARMONIC FATIGUE EVALUATION

(76) Inventor: Francis Masyada, 11415 126th Ave. N., Largo, FL (US) 33778

( * ) Notice: Subject to any disclaimer, the term of this patent is extended or adjusted under 35 U.S.C. 154(b) by 0 days.

(21) Appl. No.: 11/601,866

(22) Filed: Nov. 17, 2006

(65) Prior Publication Data

US 2007/0119254 A1 May 31, 2007

Related U.S. Application Data

(60) Provisional application No. 60/737,852, filed on Nov. 17, 2005.

(51) Int. Cl.
*G01N 29/032* (2006.01)
*G01N 29/036* (2006.01)
(52) U.S. Cl. .............. 73/579; 73/582; 73/599; 73/602
(58) Field of Classification Search ............ 73/579, 73/597, 598, 602, 582, 583, 779, 599, 600, 73/778
See application file for complete search history.

(56) References Cited

U.S. PATENT DOCUMENTS 3,916,699 A * 11/1975 Moran et al. ............ 73/623
4,968,359 A * 11/1990 Hebel et al. ............ 148/558
5,242,512 A * 9/1993 Bagley et al. ............ 148/558
6,023,975 A * 2/2000 Willis .................... 73/579
6,026,687 A * 2/2000 Jury ...................... 73/582
6,116,088 A * 9/2000 Schneider et al. ......... 73/579
6,338,765 B1 * 1/2002 Statnikov ............... 148/558
6,802,221 B2 * 10/2004 Hedeen et al. ........... 73/587
7,134,344 B2 * 11/2006 Kurt-Elli ................ 73/664
7,263,886 B2 * 9/2007 Jury ...................... 73/579

* cited by examiner

*Primary Examiner*—Hezron Williams
*Assistant Examiner*—J M Saint Surin
(74) *Attorney, Agent, or Firm*—Harness, Dickey & Pierce, P.L.C.

(57) ABSTRACT

A method and apparatus for determining the performance level, amount of wear, and remaining useful life of a new or worn object, preferably of metallic construction through harmonic fatigue evaluation. The object to be tested is struck with a resonant frequency generating device, causing the object to transmit its vibrational resonance to at least one signal receiving transducer. The transducer then relays the frequency back to a database wherein it is compared to known frequency responses of that specific object through a linear continuum from prior controlled testing, to determine the remaining performance level in comparison to a new object of the same construction.

6 Claims, 2 Drawing Sheets

HARMONIC FATIGUE EVALUATION

CROSS-REFERENCE TO RELATED APPLICATION

This application claims the benefit of U.S. Provisional Application No. 60/737,852, filed on Nov. 17, 2005. The disclosure of the above application is incorporated herein by reference.

FIELD OF THE INVENTION

The present disclosure relates to harmonic fatigue evaluation of metals, and more particularly pertains to utilizing resonance to determine the remaining useful life of a component as it begins to fatigue, wear or erode.

BACKGROUND

The statements in this section merely provide background information related to the present disclosure and may not constitute prior art.

Many metallic components such as those utilized in vehicular applications are subject to fatigue, wear, erosion, and even internal stresses which affect the components molecular structure. Nearly all structural weaknesses are related to vibrational problems associated with resonance behavior (that is the natural frequency being excited by operational forces). Detecting the amount of wear a certain component has endured has generally been by pure visual observation and measurement. The thickness of a component such as a brake rotor can be measured, and compared to original specifications, but this can only determine the amount of material which has been worn off, or still remains. These types of measurements yield no information as to the molecular structure of the component, which may have drastically changed due to micro-fractures, austenitizing or deformation. As parts wear, fatigue and/or begin to break down, the resonant frequency and/or amplitude begin to change, as well. In most cases these features show a slow and linear degradation.

Tests such as magna fluxing have been developed which can show the amount of wear and/or molecular and crystal structure changes of the component, but cannot determine the remaining performance level of the component. It is therefore desirous to have a means of determining the remaining performance level of a component, whether it is new or used, which can quickly and accurately test, record, and compare the results with a database yielding the remaining performance level of the individual component.

SUMMARY

In view of the foregoing disadvantages inherent in the known types of component testing, it is an object of the present invention to determine the remaining performance level of a component, whether new or used, by utilizing harmonic fatigue evaluation.

A further object of the present invention is to provide a harmonic fatigue evaluation comprising a portable testing device, which can easily be transported to test the integrity of an object which cannot be easily moved.

It is another object of the present invention to provide a harmonic fatigue evaluation system comprising an electronic database of known values for the various metals to be tested and allowing for comparison of the individual component results thereto.

Lastly, it is an object of the present invention to provide the above results quickly and accurately, allowing for necessary modifications or replacement of components as needed. These and other objects will become apparent from the specification wherein resonant frequency and/or amplitude of a component is utilized to determine the remaining performance level or life of that component.

As parts wear, fatigue and/or begin to break down, the resonant frequency and/or amplitude begin to change, as well. In most cases these features show a slow and linear degradation and in rare cases they may show an increase in amplitude or resonant frequency, but it is typically linear, as well. It can be shown that the complete dynamic behavior of a structure (in a given frequency range) can be viewed as a set of individual modes of vibration, each having a characteristic natural frequency, damping mode and shape.

For example, a brake rotor may show a resonant frequency of 2,500 Hz when new, but after 10,000 miles this may become 2,300 Hz and when the brake has reached its safe life, when it should be replaced, it may be 500 Hz, but the decline is generally linear.

The same effect is similar in all metals, and stress levels of new components can be determined by comparing their resonant frequency with known new parts of 'good' quality. A component to be tested is placed in a fixture (if it is feasible to remove it) specifically designed for that component. It will then be hit with a controlled impact hammer (or similar device to insure the correct pressure of the contact). One or more transducers will be placed at strategic locations on the component, to record the modal activity and excitement caused by the vibrating part. This data is then recorded electronically as resonant frequency and/or amplitudes. The combination resonant frequency and/or amplitude is then fed into a database used to compare the test results with results accumulated prior to by deliberately fatiguing components over controlled conditions.

As a component begins to fatigue, wear, erode or internal stresses are developed, the molecular structure begins to change. In some cases new materials are formed, such as when a brake rotor heats up, and austenite may be converted to hard, brittle martensite. These changes affect the resonant frequency of the object, whereas once it is compared to the known values of the database, it can determine the remaining performance level of the component.

Further areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way.

DETAILED DESCRIPTION

Figure 1:
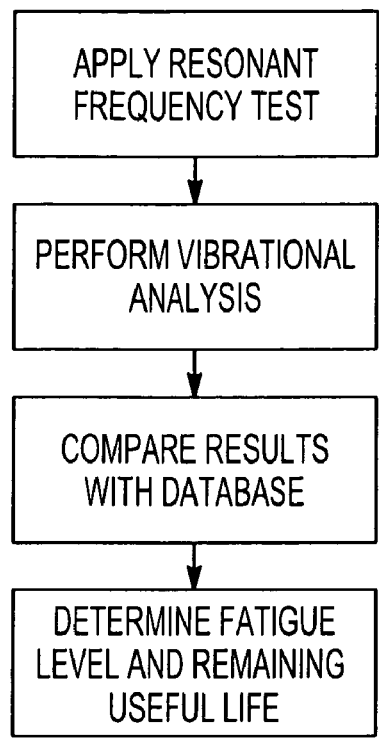
FIG. 1 is a flow diagram of the steps included in the method of the present invention.

The following description is merely exemplary in nature and is not intended to limit the present disclosure, application, or uses. It should be understood that throughout the drawings, corresponding reference numerals indicate like or corresponding parts and features.

With reference now to the drawings, and in particular to FIG. 1 thereof, the preferred embodiment of the new and improved harmonic fatigue evaluation system embodying the principles and concepts of the present invention and generally designated by the reference numeral 10 will be described.

The present invention, a system of determining the performance level of a new or used metal component through harmonic fatigue evaluation, is comprised of a plurality of components. Such components in their broadest context include a vibrational analyzer having a sending unit, a signal transducer, and a database to compare the results of the vibrational tests. Such components are individually configured and correlated with respect to each other so as to attain the desired objectives.

Figure 2:
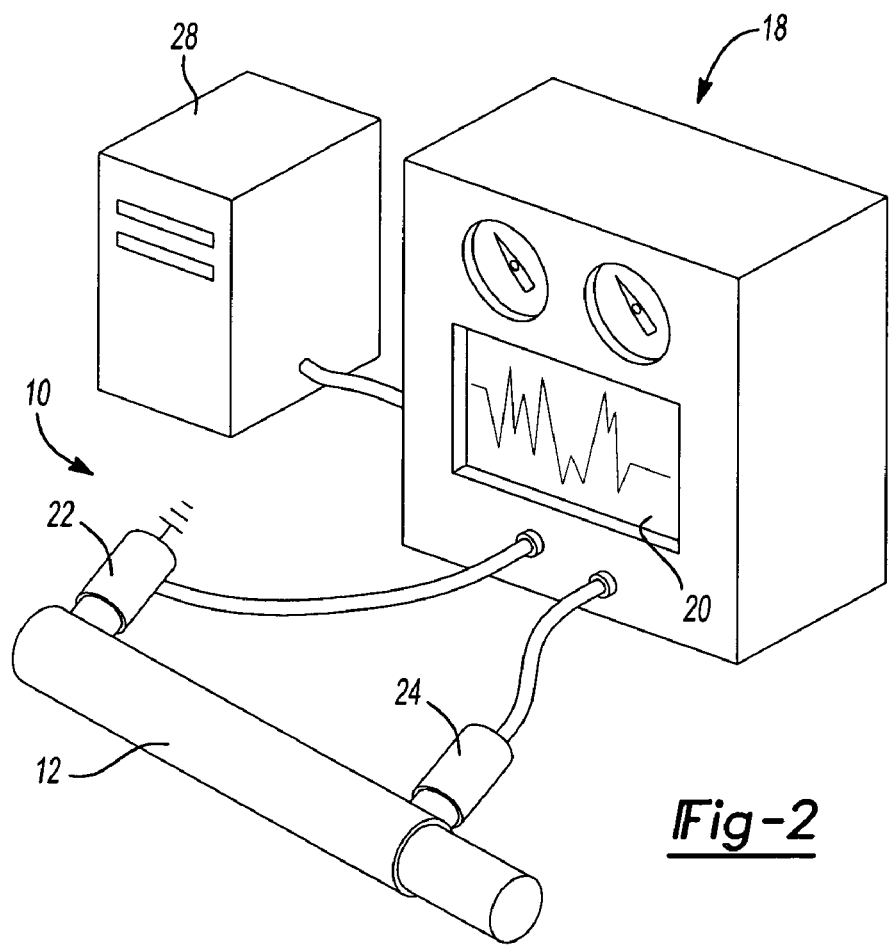
FIG. 2 is a perspective illustration of the vibration analyzer of the system of the present invention.

Referring now to FIG. 2, first provided is an object to be tested. The object has a structural resonant frequency, whether it is new or worn, and in the preferred embodiment is comprised of metal, an alloy of metal, or a combination of metals. Next provided is a vibration analyzer 18. The vibration analyzer 18 is any one of the commercially available vibration analyzers and preferably has a display screen 20. An object testing subassembly 12 is shown, which comprises a housing for holding and containing the object to be tested there within, and further comprises a signal sending component 22 and one or more signal receiving transducers 24. The signal sending component is one of the classes of sending components that includes a controlled striking member, a vibratory member, and an audio signal member for sending a signal through the object to be tested.

The object testing subassembly 12, as mentioned, has a signal receiving transducer 24 for receiving the signal and generating resonant and/or vibratory data. The signal receiving transducer couples with the object to be tested.

The harmonic fatigue evaluation system 10 has a data collection subsystem 28 to which it is coupled, such as a computer or other memory device, for receiving, storing and comparing the data received from the resonant testing of the object. The coupling between the data collection subsystem and the vibration analyzer 18 is a coupling selected from the class of couplings including electronic, radio frequency, and optical. The data carried in the preferred embodiment is digital, but in an alternative embodiment may be transmitted in analog. The sending component sends a signal through the object and the receiving component picks up the signal after it has passed through the object.

Figure 3:
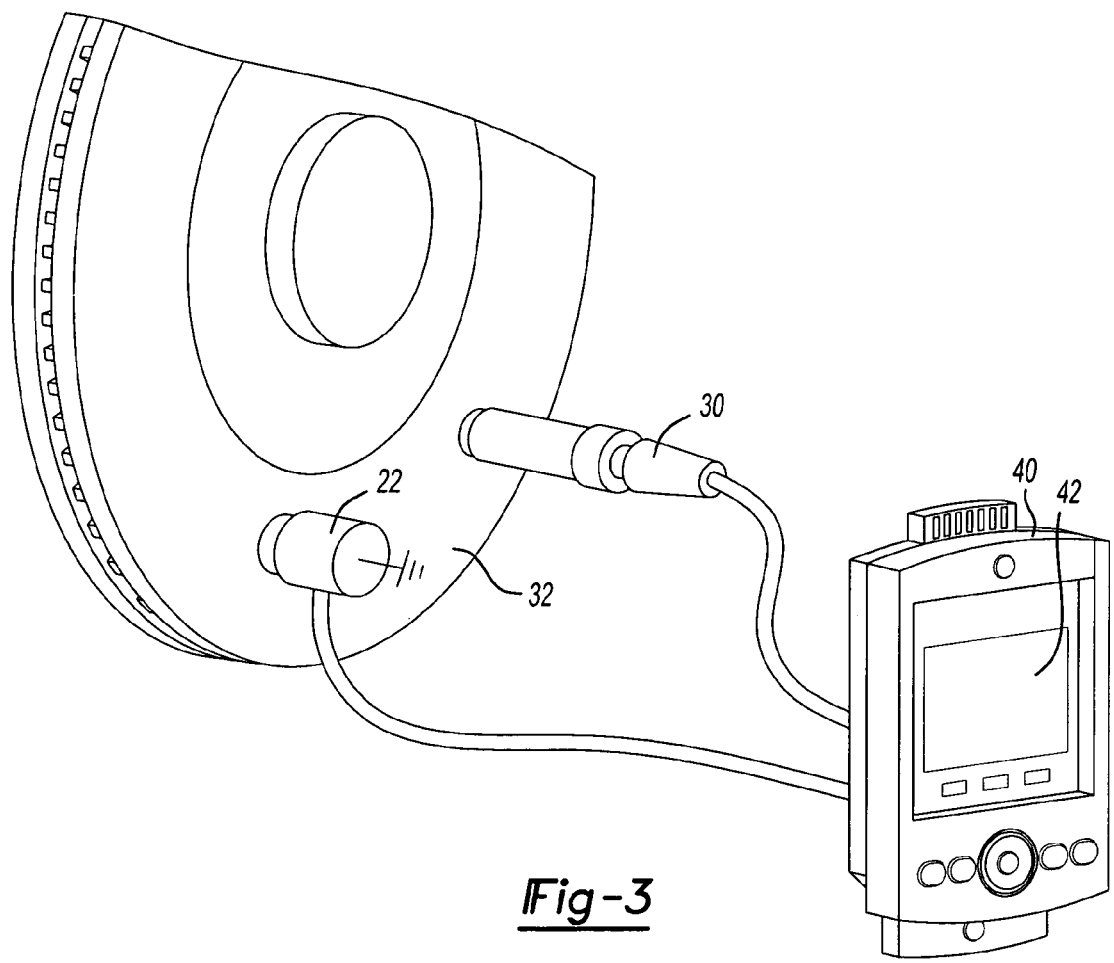
FIG. 3 is a perspective illustration of a portable resonant frequency recording device utilized in conjunction with a transducer placed upon a brake rotor.

In an alternative embodiment, illustrated in FIG. 3, the harmonic fatigue evaluation system 10 can be used to remotely test the resonant frequency and/or amplitude of objects that cannot be removed and placed within an object testing subassembly, such as a brake rotor 32 attached to an axle, as shown. In the alternative, a mobile data acquisition device 40, preferably having a display 42 known in the art, is connected to the receiving transducer 30, which attaches directly to the object 32. A signal sending component 22, as outlined above, generates a signal to be received as data by the transducer 30. Once the data is generated and stored within the mobile device 40, it can then be relayed later in time to a data collection subsystem by coupling the data acquisition device directly to a data collection subsystem, or possibly transmitting the collected data by radio frequency, as mentioned above, for analysis and comparison with known data within the database.

The data collected from multiple samples of varying metals and objects will form the database upon which testing data is compared, to determine the remaining performance level of the object in question. With respect to the description herein, it is to be realized that the optimum dimensional relationship for the parts of the invention, to include variations in size, materials, shape, form function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered illustrative only of the principles of the invention. Further, since numerous modifications and changes will readily occur to those skilled in the art, it is not desired to limit the invention to the exact construction and operation shown and described and, accordingly, all suitable modifications and equivalents may be resorted to, falling within the scope of the invention.

What is claimed is:

1. A harmonic fatigue evaluation system for determining the fatigue of metallic objects comprising:
   a vibration analyzer, said vibration analyzer comprising a processor and electronic database for storage and comparison of data;
   a signal receiving transducer, said signal receiving transducer being attached to a metallic object to be tested for fatigue and comprises a coupling means to attach said receiving transducer to said vibration analyzer; and
   a signal sending unit, said signal sending unit being attached to a metallic object at a predetermined distance from said signal receiving transducer, said signal sending unit being in communication with said vibration analyzer to transmit a signal from said vibration analyzer to said metallic object;
   wherein said vibration analyzer relays a signal to said signal sending unit to generate a signal onto said metallic object, said metallic object responding to the signal by means of harmonic vibrations, said signal receiving transducer receiving said harmonic vibrations in the form of frequency and amplitude indicative of a resonant frequency of the metallic object and transmitting said signal as data through said coupling means to said vibration analyzer, said vibration analyzer adapted to receive said data for a subsequent comparison of said resonant frequency of the metallic object to prerecorded data within said database having a plurality of resonant frequencies of a new component and multiple deliberately fatigued components over controlled conditions, reduction of the resonant frequency of the metallic object indicating when the metallic object requires replacement.

2. The harmonic fatigue evaluation system of claim 1, wherein said signal sending unit comprises a signal sending component from the class of: striking members, vibratory members, and audio signal members.

3. The harmonic fatigue evaluation system of claim 1, wherein said data transmitted through said coupling means is digital.

4. The harmonic fatigue evaluation system of claim 1, wherein said data transmitted through said coupling means is analog.

5. The harmonic fatigue of claim 1, wherein said coupling means transmits data from said signal receiving transducer to said vibration analyzer in the form of one of the following signals: electronic, radio frequency, optical.

6. A method of testing the fatigue of a metallic object comprising the steps of:

(a) attaching a signal sending unit to said metallic object, said signal sending unit comprising a controlled signal generator attached to a vibration analyzer;
(b) attaching a signal receiving transducer to said metallic object, a predetermined distance away from said signal sending unit, said signal receiving transducer being attached to said vibration analyzer, and receives signals in the form of varied vibrational frequency and amplitude;
(c) inducing said vibration analyzer to generate a signal to said signal sending unit, said signal generator of said signal sending unit inducing a signal upon said metallic object in the form of harmonic vibration by means of striking said metallic object in a controlled manner indicative of a resonant frequency of said metallic object; and
(d) measuring the frequency and amplitude of said vibration by means of said signal receiving transducer relaying said signals to said vibration analyzer;
said vibration analyzer comparing said resonant frequency with a database of parameters specific for said metallic object including resonant frequencies of deliberately fatigued components to determine fatigue of said metallic object.

* * * * *